United States Patent
Goldstein

(10) Patent No.: US 11,223,919 B2
(45) Date of Patent: Jan. 11, 2022

(54) FIXATION METHODS FOR TRAVERSING EAR CANALS

(71) Applicant: Steven Wayne Goldstein, Delray Beach, FL (US)

(72) Inventor: Steven Wayne Goldstein, Delray Beach, FL (US)

(73) Assignee: STATON TECHIYA, LLC, Delray Beach, FL (US)

( * ) Notice: Subject to any disclaimer, the term of this patent is extended or adjusted under 35 U.S.C. 154(b) by 277 days.

(21) Appl. No.: 14/956,365

(22) Filed: Dec. 1, 2015

(65) Prior Publication Data

US 2016/0157031 A1    Jun. 2, 2016

Related U.S. Application Data

(60) Provisional application No. 62/086,019, filed on Dec. 1, 2014.

(51) Int. Cl.
*A61F 11/00* (2006.01)
*H04R 25/00* (2006.01)

(52) U.S. Cl.
CPC ............ *H04R 25/656* (2013.01); *A61F 11/00* (2013.01); *H04R 25/659* (2019.05); *A61F 2250/0001* (2013.01); *A61F 2250/0018* (2013.01); *A61F 2250/0045* (2013.01); *H04R 2225/023* (2013.01)

(58) Field of Classification Search
CPC .............................................. A61F 2250/0003
See application file for complete search history.

(56) References Cited

U.S. PATENT DOCUMENTS

| 5,415,633 | A | * | 5/1995 | Lazarus | A61M 25/0158 |
| | | | | | 600/434 |
| 5,904,657 | A | * | 5/1999 | Unsworth | A61M 25/09 |
| | | | | | 600/585 |
| 7,947,071 | B2 | | 5/2011 | Schmid et al. | |
| 7,963,288 | B2 | | 6/2011 | Rosenberg et al. | |
| 8,353,948 | B2 | | 1/2013 | Besselink et al. | |
| 8,545,547 | B2 | | 10/2013 | Schmid et al. | |
| 9,066,827 | B2 | | 6/2015 | Schmid et al. | |
| 9,125,740 | B2 | | 9/2015 | Morriss et al. | |
| 2003/0236445 | A1 | * | 12/2003 | Couvillon, Jr. | A61M 25/0105 |
| | | | | | 600/114 |

(Continued)

OTHER PUBLICATIONS

Manfredo P. DO Carmo, Differential Geometry of Curves and Surfaces, 1976, p. 19, Prentice-Hall, Inc. Englewood Cliffs, New Jersey, US.

*Primary Examiner* — Jacqueline Woznicki
(74) *Attorney, Agent, or Firm* — Akerman LLP; Peter A. Chiabotti

(57) ABSTRACT

A method and system of traversing a device through an accommodating conduit to reach a target area within the accommodating conduit can include varying an amount of elasticity of the device or an amount of torsion moment of the device applied to the accommodating conduit or varying both to minimize bending forces as the device traverses the accommodating conduit. The method or system upon reaching the target area within the accommodating conduit, can further include varying the elasticity or the torsion moment of the device or varying both to cause the device to stiffen. Other embodiments are disclosed.

2 Claims, 5 Drawing Sheets

(56) References Cited

U.S. PATENT DOCUMENTS

| | | | | |
|---|---|---|---|---|
| 2005/0033343 A1* | 2/2005 | Chermoni | ......... | A61M 25/0122 |
| | | | | 606/191 |
| 2007/0197906 A1* | 8/2007 | Ritter | ................ | A61M 25/0158 |
| | | | | 600/424 |
| 2007/0250149 A1* | 10/2007 | Von Oepen et al. | ... | A61F 2/958 |
| | | | | 623/1.11 |
| 2014/0200661 A1 | 7/2014 | Pintor et al. | | |

* cited by examiner

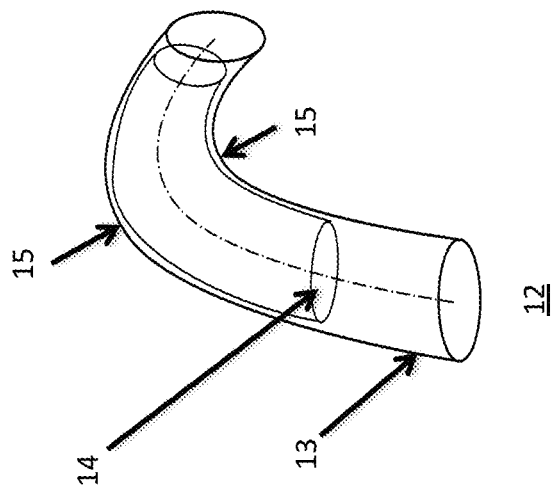
FIG. 1B
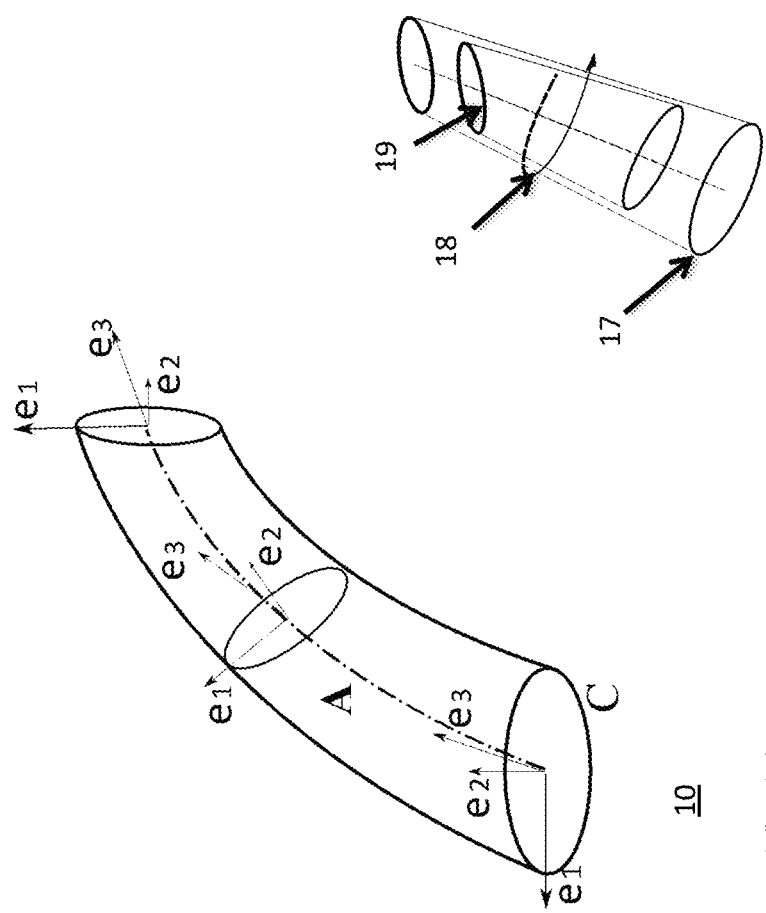
FIG. 1C
FIG. 1A

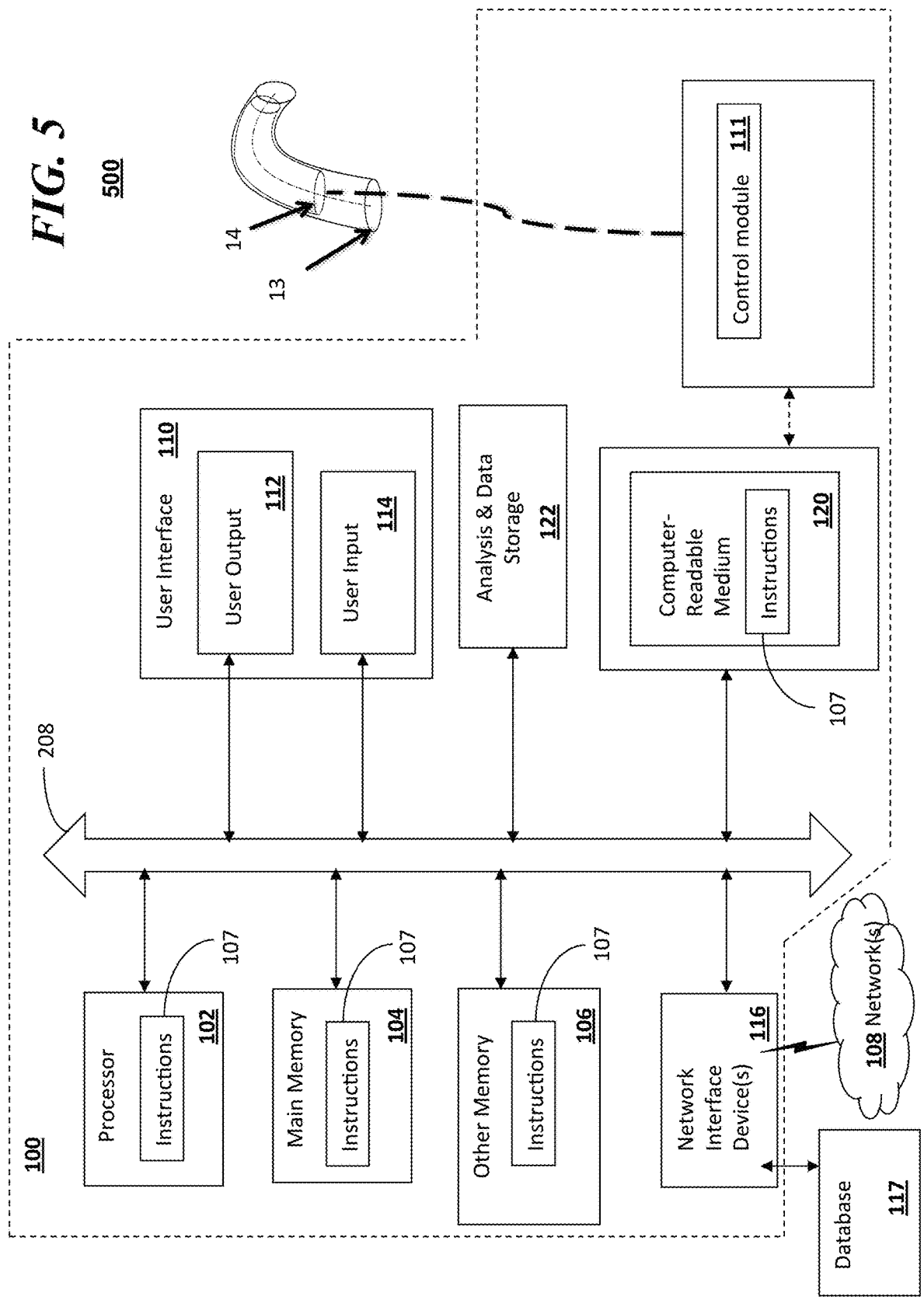

FIXATION METHODS FOR TRAVERSING EAR CANALS

CROSS REFERENCE TO RELATED APPLICATIONS

This application claims the priority benefit of Provisional Application No. 62/086,019 filed on Dec. 1, 2014, the entire contents and disclosure of which are incorporated herein by reference.

FIELD

The present disclosure pertains to fixation methods and devices within tubular structures, and more particularly, to fixation methods and devices for miniature medical devices in tubular structures.

BACKGROUND

Rapid miniaturization of medical devices is about to revolutionize the whole medical field. Smart devices are currently being designed for insertion into the human body for diagnostics, monitoring, drug delivery and in the future for treatment, quality of life enhancements and even surgery. At the same time, certain new challenges need to be overcome to make those devices safe and effective. One of the first problems that occur is a stable fixation of the device inside human body. Implantable devices are often permanently attached to the anatomical structures and cannot be easily removed or repositioned. This approach is not applicable when the device needs to travel inside the body or be inserted with minimal surgical impact. One example of a device that travels inside the body that does not necessarily require fixation is the Given Imaging PillCam®, that traverses the digestive system and transmits real time video to the operator. Another example of a device that does not necessarily require fixation is a device that is frequently inserted and released as with in-the-ear devices.

Tubular structures are very common in human body. Current solutions (i.e. cardio-vascular stents) apply radial forces on the walls to increase friction with tissue and avoid mutual motion. With this approach, however, the tissue is under perpetual pressure, which is usually not desirable. Tissue necrosis is often experienced from long-term radial force within a biological lumen.

A method and device that mitigates or avoids most or all of the issues described above is unknown.

SUMMARY

Embodiments in accordance with the present disclosure provides a fixation method and fixation devices for miniature medical devices in tubular structures.

A novel approach to stable fixation of miniature devices in tubular structures can include a key idea to utilize curvature or torsion or both that often naturally occur in organic shapes due to certain tissue growth mechanisms. [See Thompson, "On Growth and Form"]. Intuitively speaking, torsion is the amount of axial rotation that occurs in the tubular structure and curvature is the amount of bending. In order to provide a more formal definition, the concept of a moving frame is introduced herein.

With respect to a moving frame with reference to FIG. 1A, a general tubular shape 10 can be described in terms of its axial curve A(s), where s is the arc-length, and the generating cross-section contour C. The resulting structure can be conveniently described by associating a moving frame E(s) ($e_1, e_2, e_3$) to each point on the axial curve A (see again, FIG. 1A). Then, the curvature $\kappa(s)$ and torsion $\tau(s)$ of the tubular shape 10 can be evaluated as angles of rotation of the moving frame. A Frenet frame is most frequently used in differential geometry [See DoCarmo, "Differential Geometry"]. This frame is defined by tangent T(s), normal N(s) and bi-normal B(s) of the axial curve.

Thus, curvature and torsion can be evaluated using Frenet-Serret formulae as follows:

$$\frac{dT}{ds} = \kappa N$$

$$\frac{dN}{ds} = -\kappa T + \tau B$$

$$\frac{dB}{ds} = -\tau N$$

While having some advantages, Frenet frame is undefined in regions of unstable second derivative. Therefore, in many practical applications minimal rotation frame (MRF) is more appropriate. Unlike with Frenet frame, MRF cannot be defined locally. It is rather defined globally by minimizing an amount of rotation between boundary conditions defined on A. In other words, it provides the transformation of the frame from the initial to final position with minimal rotation around A.

Curvature and torsion are intrinsic properties of the curve and therefore invariant under Euclidean transformations. Consequently, those properties are independent of the reference system of coordinates. It is also known that any curve in space can be uniquely identified by its curvature $\kappa(s)$ and torsion $\tau(s)$ defined on the curve [DoCarmo, Differential Geometry]. Or more formally, two curves are congruent if and only if their $\kappa(s)$ and $\tau(s)$ are identical. In practice, if the curves are smooth, it is sufficient to require identity of intrinsic properties in a limited number of points in order to guarantee congruency. This observation provides the basis for the proposed fixation methods described in the following section.

The proposed fixation methods are based on forces of friction and elasticity. The idea is inspired by locomotion of organisms such as worms and snakes inside narrow tunnels. In this invention, three different methods are proposed. Each method is suitable for certain combination of the intrinsic properties of the tubular structure introduced above. The following table summarizes all possible combinations of the intrinsic properties.

| Method | Curvature | Torsion |
|---|---|---|
| 1 | Yes | No |
| 2 | No | Yes |
| 3 | Yes | Yes |

BRIEF DESCRIPTION OF THE DRAWINGS

FIG. 1A is a pictorial diagram of a moving frame in accordance with an exemplary embodiment;

FIG. 1B is a pictorial diagram of a tubular structure exhibiting bending following a curvature profile in accordance with an exemplary embodiment;

FIG. 1C is a pictorial diagram of a tubular structure exhibiting rotation around an axial curve that produces torsion in accordance with an exemplary embodiment;

FIG. 5 is a block diagram of a system in accordance with an embodiment herein.

DETAILED DESCRIPTION

Figure 2:
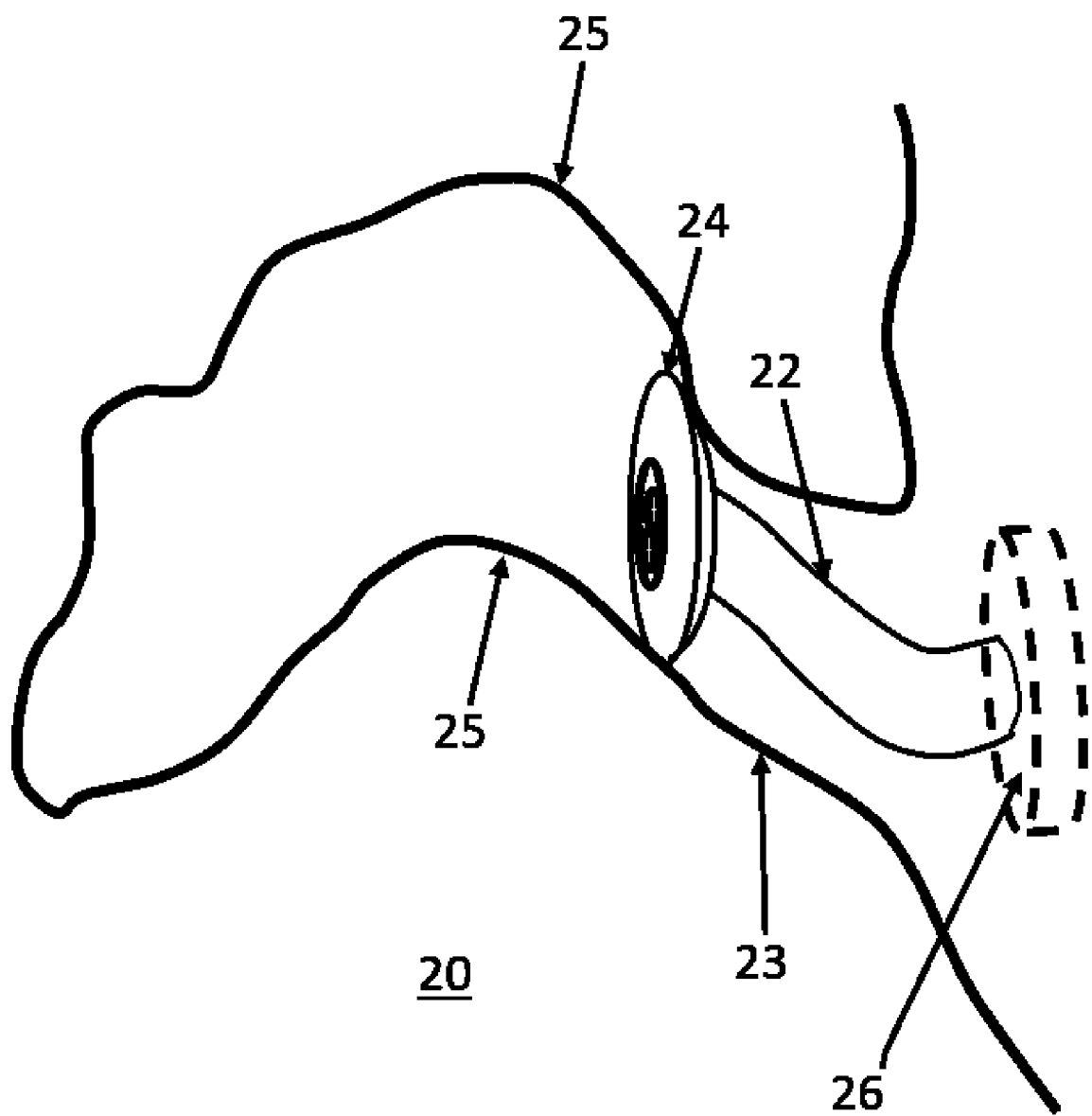
FIG. 2 is a pictorial diagram of an elliptical balloon in an ear canal.

Methods and devices in accordance with the embodiments are not limited to exact methods disclosed and variations within contemplation of the embodiments can certainly include variations that include one or more methods in combination and steps in methods that are skipped, or completed in different order or additional steps beyond the steps disclosed herein.

Method #1.

When a tubular structure 13 is bending at a bend 15 as illustrated in a system 12 of FIG. 1B, it is proposed in some embodiments to vary the elasticity of a device 14 in order to achieve fixation. When the device 14 is traveling through the accommodating structure 13, the device 14 can be very flexible and can be configured to not apply any bending forces on the structure 13. Once the device 14 will arrive to the desired location, the device can be configured to become stiff and follow the curvature profile (15) of the tubular structure. This effect can be achieved for example by using mechanical interlocking or electro-magnetic forces, electro-activated polymers, or with the introduction of gas or fluid into the tubular structure with an additional ability to regulate the operating pressure of the fluid in the tubular structure. As a result, the device 14 will be immobilized in its current position and shape within the biological lumen at a desired location. Stability of the device 14 may be controlled through the amount of bending force applied on the accommodating structure 14.

FIG. 1B illustrates a method of traversing a device 14 through an accommodating conduit (such a biological lumen) 13 to reach a target area within the accommodating conduit. In one example, the target area can coincide with a bend 15 in the structure 13. In some embodiments, the method can include varying an elasticity of the device to minimize bending forces as the device traverses the accommodating conduit and upon reaching the target area within the accommodating conduit, further varying the elasticity of the device to cause the device to stiffen. In some embodiments the method further follows a curvature profile of the accommodating conduit at a target area when the device is caused to stiffen. As noted above, varying the elasticity of the device can be done by any number of techniques, for example, using mechanical interlocking forces, using electro-magnetic forces, using electro-activated polymers (EAPs), or by introducing one of gas or fluid into the device with an additional ability to regulate the operating pressure of the fluid in the device.

In some embodiments, the device 14 can be immobilized in its current position and shape within the accommodating conduit 13 at the target area. Additionally, a stability of the device is controlled through an amount of bending force applied on the accommodating conduit.

A device 14 in some embodiments can include one or more members of the device having a controllable elasticity where the device is configured to traverse an accommodating conduit 13 (such as a biological lumen, e.g., artery, vein, etc.). The device 14 can include or be operatively coupled to a controller or processor (such as processor 102 or control module 111 of FIG. 5) for controlling the controllable elasticity of the device as the device traverses the accommodating conduit towards a target area of the accommodating conduit and for further causing one or more members of the device to selectively stiffen as the device reaches the target area. As noted above, such a device can include mechanical interlocking members that apply mechanical interlocking forces, or use electro-magnetic members that applying electro-magnetic forces, or use electro-activated polymers (EAPs). In some embodiments, the controller controls the introduction of one of gas or fluid into the device with an additional ability to regulate the operating pressure of the fluid in the device.

Method #2.

When a tubular structure 17 is rotating around its axial curve producing torsion, fixation can be achieved by utilizing torsional moment 18 as illustrated in system 16 of FIG. 1C. Similar to Method #1, a device 19 can be very flexible during insertion. Once in place, the device 19 will constrain two or more cross-sections in their relative orientation, following the torsion of the tubular structure. This can be done using inflatable balloons (see device 24 of FIG. 2) which are created to fit within the geometry of the cross section, or by extending supports into walls of the tubular structure. With this method, stability of the device can be controlled by varying the amount of torsion moment applied on the accommodating structure. The balloons are to be adhered, molded or otherwise affixed to the tubular structure in alignment or in misalignment based on the amount of torsion and ultimate fixation required.

In some embodiments and referring again to FIG. 1C, a method of traversing a device 19 through an accommodating conduit 17 (such a biological lumen) to reach a target area within the accommodating conduit can include the steps of varying an amount of torsion moment of the device 19 applied to the accommodating conduit 17 to minimize bending forces as the device traverses the accommodating conduit 17 and upon reaching the target area within the accommodating conduit, further varying the torsion moment of the device 19 to cause the device 19 to stiffen. In some embodiments, varying the amount of torsion moment of the device applied to the accommodating conduit can be done by using inflatable balloons configured to fit within a geometry of a cross section of the accommodating conduit. In some embodiments, varying the amount of torsion moment of the device applied to the accommodating conduit can alternatively be done by using support members that extend into the walls of a tubular structure of the device. A stability of the device can also be controlled through an amount of torsion moment applied on the accommodating conduit.

A device 19 in some embodiments can include one or more members of the device having a controllable torsion moment of the device where the device is configured to traverse an accommodating conduit 17 (such as a biological lumen, e.g., artery, vein, etc.). The device 19 can include or be operatively coupled to a controller or processor (such as processor 102 or control module 111 of FIG. 5) for controlling the controllable torsion moment of the device as the device traverses the accommodating conduit 17 towards a target area of the accommodating conduit 17 and for further causing on or more members of the device to selectively stiffen as the device reaches the target area. In some embodiments, the controllable torsion moment of the device 19 is controlled by using one or more inflatable balloons (see device 24 of FIG. 2) configured to fit within a geometry of a cross section of the accommodating conduit. In some embodiments, the one or more inflatable balloons can be affixed to a tubular structure of the device in alignment or in misalignment with the accommodating conduit based on the amount of torsion and ultimate fixation desired at the target area. In some embodiments, the controllable torsion moment of the device is controlled by using support members that extend into the walls of a tubular structure of the device.

Method #3.

When the tubular structure of interest has a helical shape, where both curvature and torsion occur, it is possible to utilize both fixation methods (Method #1 and Method #2) described above simultaneously. In such an instance, which often occurs in human body, increased fixation can be achieved. One particular example of such structure, the external auditory canal (EAC), is discussed in detail further below. However, a method in accordance with the embodiments is not limited to using both fixation methods simultaneously. As contemplated herein, either method can be used either alone or in a serial fashion or simultaneously as appropriately suited for a given structure and application.

Thus, in some exemplary embodiments, a method of traversing a device through an accommodating conduit (such a biological lumen) to reach a target area within the accommodating conduit can include varying an amount of elasticity of the device OR varying an amount of torsion moment of the device applied to the accommodating conduit OR varying both (elasticity and torsion moment) to minimize bending forces as the device traverses the accommodating conduit. Upon reaching the target area within the accommodating conduit, the method can further vary the elasticity OR vary the torsion moment of the device (OR vary both) to cause the device to stiffen. As note above, in some embodiments the step of varying comprises varying the amount of elasticity AND the amount of torsion moment of the device and further varying the elasticity or the torsion moment of the device (or varying both) upon reaching the target area.

A device in some embodiments can include one or more members of the device having a controllable elasticity of the device OR a controllable torsion moment of the device, where the device is configured to traverse an accommodating conduit (such as a biological lumen, e.g., artery, vein, etc.). As in other embodiments, the device can also include a controller or processor for controlling the controllable elasticity OR the controllable torsion moment of the device (or both) as the device traverses the accommodating conduit towards a target area of the accommodating conduit and for further causing one or more members of the device to selectively stiffen as the device reaches the target area.

One particular accommodating conduit that can be used as an example for fixation of devices is the fixation of devices in the external auditory canal (EAC). In recent years, completely-in-the-canal (CIC) devices became main stream in the hearing aid industry. The smaller and smarter those devices become, the wider range of possible applications opens. Currently, CIC devices are personalized for each customer, so the tight fit guarantees device stability in the ear. However, as electronic components and manufacturing technologies evolve, it is becoming possible to come up with one-fits-most designs which will be suitable for almost anyone. Consequently, new fixation techniques are developed herein to ensure reliable device positioning.

The EAC has a cross section of an elliptical shape near the orifice that gradually converges towards the tympanic membrane. The axial curve of the canal has two distinctive high curvature regions, known as 1st and 2nd bends, as can be seen in in the illustration 20 of FIG. 2. The EAC is an example of an accommodating structure 23 that has at least one bend 25. A device 24 such as a balloon attached to an insertion member or stem 22 is illustrated as the balloon traverses the accommodating structure 23. Our research has shown that the average axial frame rotation between the orifice (or opening of the ear) and the 1st bend is about 30 degrees, shown in the illustration 30 of FIG. 3. The intertragal notch is illustrated on illustration 30 as a reference point. This rotation can be leveraged for secure fixation of CIC devices in the ear based on a desired insertion depth. With the proposed embodiments, the device in some embodiments can be equipped with an elliptical balloon on the canal side and stopping ring or a flange or another balloon on the orifice side. During the insertion, the balloon can slightly rotate around the axis. However, once the device is inserted, the rotation angle is fixed and due to the difference between actual canal angle of rotation and the one imposed by the device, a moment will be applied by the tissue on the balloon. This moment will prevent the device from accidentally escaping out of the ear canal. The fixed angle of rotation can be modified by the wearing person once the device is inserted in order to increase or decrease the locking moment.

In addition, curvature of the ear canal can be utilized to provide even more secure fixation. In order to achieve such greater secure fixation, the device should have a flexible body. After insertion, the shape of the device will adapt to the accommodating ear and fix. Similar to the rotation, bending of the device can be controlled by the user to maximize comfort and reliability.

Figure 3:
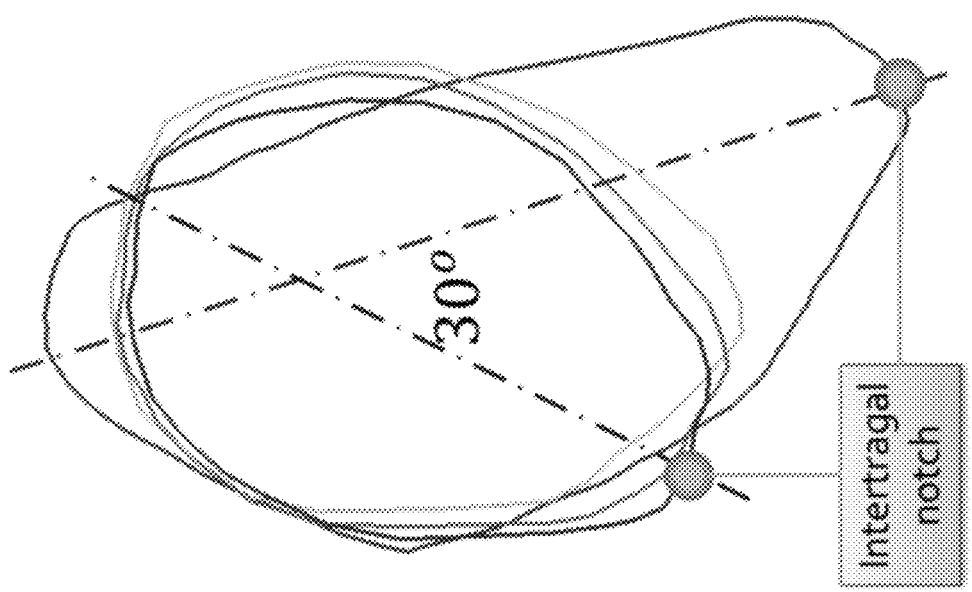
FIG. 3 is an ear canal cross section rotation in accordance with an embodiment.

In a some embodiments as illustrated in FIG. 2 where a device 24 is configured for placement in an external auditory canal 23, such fixation device can include an elliptical shaped balloon on a distal end of an insertion member 22. In some embodiments the device 24 is a flexible body member. In some embodiments, the device 24 can include a flange or stopping ring or another balloon 26 on a proximal end of the insertion member 22. During insertion of the fixation device in the EAC, the elliptical shaped balloon rotates around an axial curve of the EAC and a rotation angle of the balloon is fixed at an angle defined by a difference between an actual canal angle of rotation and an angle imposed by the fixation device causing a locking moment applied by a tissue of the EAC on the balloon. In some embodiments, the locking moment is further modified by a user of the fixation device.

Figure 4:
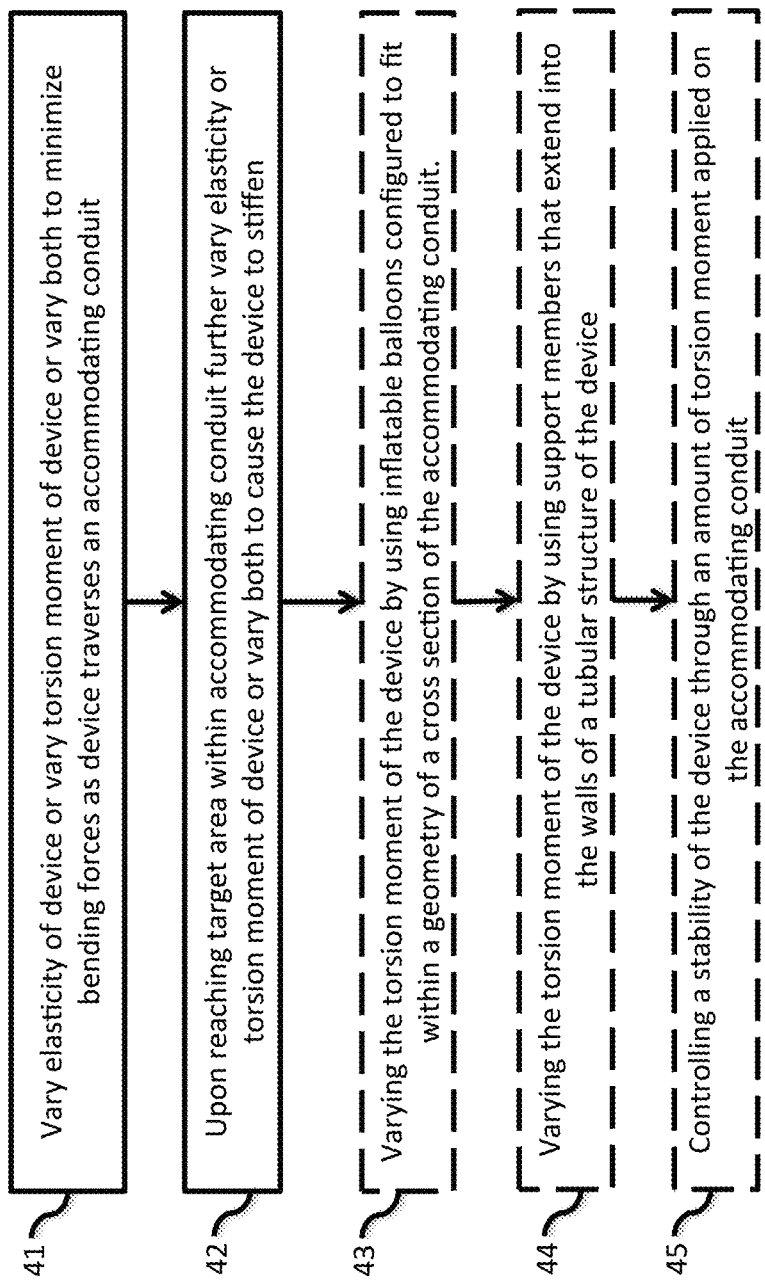
FIG. 4 is a flowchart for a fixation method in accordance with an exemplary embodiment.

Referring to FIG. 4, a method 40 of traversing a device through an accommodating conduit to reach a target area within the accommodating conduit can include the step 41 of varying an amount of elasticity of the device or an amount of torsion moment of the device applied to the accommodating conduit or varying both to minimize bending forces as the device traverses the accommodating conduit and the step 42 of further varying the elasticity or the torsion moment of the device or varying both to cause the device to stiffen upon reaching the target area within the accommodating conduit. The embodiments can encompass variations as exemplified by the claims. In some embodiments, the method 40 can vary the torsion moment of the device by using at least one inflatable balloon configured to fit within a geometry of a cross section of an accommodating conduit as shown at step 43. In some embodiments, the method 40 can vary the torsion moment of the device by using support members that extend into the walls of a tubular structure of the device as in step 44. In some embodiments, the method 40 can include the step 45 of controlling a stability of the device through an amount of torsion moment applied on the accommodating conduit.

Referring FIG. 5, an information processing system 100 or other system 500 can be communicatively coupled with a module 111 for controlling elasticity or the torsion moment of a device 14 as it traverses a structure 13 and subsequently is put in a target area within the structure 13 as described in the aforementioned methods above. According to this example, at least one processor 102, responsive to executing instructions 107, performs operations to communicate with the module 111 via a bus architecture 208, as shown. The at least one processor is communicatively coupled with main memory 104 or other memory 106, and a computer readable medium 120. The processor is communicatively coupled with an Analysis & Data Storage 122 that, according to various implementations, can maintain stored information used by, for example, the module 111 and more generally used by the information processing system. Additionally, according to another example, an history or repository of shapes or structures can be maintained or stored in the Analysis & Data Storage. The module 111, and the information processing system 100, can use the information from the storage 122.

The information processing system includes a user interface 110 that comprises a user output interface 112 and user input interface 114. Examples of elements of the user output interface can include a display, a speaker, one or more indicator lights, one or more transducers that generate audible indicators, and a haptic signal generator. Examples of elements of the user input interface can include a keyboard, a keypad, a mouse, a track pad, a touch pad, a microphone that receives audio signals. The received audio signals, for example, can be converted to electronic digital representation and stored in memory, and optionally can be used with voice recognition software executed by the processor to receive user input data and commands.

A network interface device 116 is communicatively coupled with the processor 102 and provides a communication interface for the information processing system to communicate via one or more networks 108. The networks can include wired and wireless networks, and can be any of local area networks, wide area networks, or a combination of such networks. For example, wide area networks including the internet and the web can inter-communicate the information processing system with other one or more information processing systems that may be locally, or remotely, located relative to the information processing system. It should be noted that mobile communications devices, such as mobile phones, Smart phones, tablet computers, phablets, lap top computers, and the like, which are capable of at least one of wired and/or wireless communication, are also examples of information processing systems within the scope of the present disclosure. The network interface device 116 can provide a communication interface for the information processing system to access the database 117 according to various embodiments of the disclosure.

The instructions, according to the present example, include instructions for performing the functions described with respect to the flow chart of FIG. 4 or other methods described herein. It should be noted that any portion of the instructions can be stored in a centralized information processing system or can be stored in a distributed information processing system, i.e., with portions of the system distributed and communicatively coupled together over one or more communication links or networks.

The present invention may be a system, a method, and/or a computer program product. The computer program product may include a computer readable storage medium (or media) having computer readable program instructions thereon for causing a processor to carry out aspects of the present invention.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer readable program instructions described herein can be downloaded to respective computing/processing devices from a computer readable storage medium or to an external computer or external storage device via a network or networks, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described herein with reference to flowchart illustrations and/or block diagrams of methods, apparatus (systems), and computer program products according to embodiments of the invention. It will be understood that each block of the flowchart illustrations and/or block functional diagrams, and combinations of blocks in the flowchart illustrations and/or block functional diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or functional block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the computer readable storage medium is shown in an example embodiment to be a single medium, the term "computer readable storage medium" should be taken to include a single medium or multiple media (e.g., a centralized or distributed database, and/or associated caches and servers) that store the one or more sets of instructions. The term "computer-readable storage medium" shall also be taken to include any non-transitory medium that is capable of storing or encoding a set of instructions for execution by the machine and that cause the machine to perform any one or more of the methods of the subject disclosure.

The term "computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a computer-readable storage medium, as listed herein and including art-recognized equivalents and successor media, in which the software implementations herein are stored.

Although the present specification may describe components and functions implemented in the embodiments with reference to particular standards and protocols, the disclosure is not limited to such standards and protocols. Each of the standards represents examples of the state of the art. Such standards are from time-to-time superseded by faster or more efficient equivalents having essentially the same functions.

The illustrations of examples described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. The examples herein are intended to cover any and all adaptations or variations of various embodiments. Combinations of the above embodiments, and other embodiments not specifically described herein, are contemplated herein.

The Abstract is provided with the understanding that it is not intended to be used to interpret or limit the scope or meaning of the claims. In addition, in the foregoing Detailed Description, various features are grouped together in a single example embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

Although only one processor is illustrated for an information processing system, information processing systems with multiple CPUs or processors can be used equally effectively. Various embodiments of the present disclosure can further incorporate interfaces that each includes separate, fully programmed microprocessors that are used to off-load processing from the processor. An operating system (not shown) included in main memory for the information processing system may be a suitable multitasking and/or multiprocessing operating system, such as, but not limited to, any of the iOS, Linux, UNIX, Windows, and Windows Server based operating systems. Various embodiments of the present disclosure are able to use any other suitable operating system. Various embodiments of the present disclosure utilize architectures, such as an object oriented framework mechanism, that allows instructions of the components of operating system (not shown) to be executed on any processor located within the information processing system. Various embodiments of the present disclosure are able to be adapted to work with any data communications connections including present day analog and/or digital techniques or via a future networking mechanism.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "another", as used herein, is defined as at least a second or more. The terms "including" and "having," as used herein, are defined as comprising (i.e., open language). The term "coupled," as used herein, is defined as "connected," although not necessarily directly, and not necessarily mechanically. "Communicatively coupled" refers to coupling of components such that these components are able to communicate with one another through, for example, wired, wireless or other communications media. The terms "communicatively coupled" or "communicatively coupling" include, but are not limited to, communicating electronic control signals by which one element may direct or control another. The term "configured to" describes hardware, software or a combination of hardware and software that is adapted to, set up, arranged, built, composed, constructed, designed or that has any combination of these characteristics to carry out a given function. The term "adapted to" describes hardware, software or a combination of hardware and software that is capable of, able to accommodate, to make, or that is suitable to carry out a given function.

The terms "controller", "computer", "processor", "server", "client", "computer system", "computing system", "personal computing system", "processing system", or "information processing system", describe examples of a suitably configured processing system adapted to implement one or more embodiments herein. Any suitably configured processing system is similarly able to be used by embodiments herein, for example and not for limitation, a personal computer, a laptop personal computer (laptop PC), a tablet computer, a smart phone, a mobile phone, a wireless communication device, a personal digital assistant, a workstation, and the like. A processing system may include one or more processing systems or processors. A processing system can be realized in a centralized fashion in one processing system or in a distributed fashion where different elements are spread across several interconnected processing systems.

The corresponding structures, materials, acts, and equivalents of all means or step plus function elements in the claims below are intended to include any structure, material, or act for performing the function in combination with other claimed elements as specifically claimed. The description herein has been presented for purposes of illustration and description, but is not intended to be exhaustive or limited to the examples in the form disclosed. Many modifications and variations will be apparent to those of ordinary skill in the art without departing from the scope of the examples presented or claimed. The disclosed embodiments were chosen and described in order to explain the principles of the embodiments and the practical application, and to enable others of ordinary skill in the art to understand the various embodiments with various modifications as are suited to the particular use contemplated. It is intended that the appended claims below cover any and all such applications, modifications, and variations within the scope of the embodiments.

What is claimed is:

1. A method of traversing a device through an accommodating ear canal conduit to reach a target area within the accommodating ear canal conduit comprising:
   inserting a device into the accommodating ear canal conduit, wherein the device includes a balloon configured to change a torsion moment of the device about it's axial curve to support movement to the target area, wherein the torsion moment of the device is applied to the accommodating ear canal conduit and wherein the device further includes a stem attached to the balloon and a flange, wherein the balloon has fluid located therewithin, wherein the stem further includes an electroactive polymer element;
   changing the torsion moment of the device by varying the operating pressure of the fluid within the balloon when the device is at the target area,
   wherein a processor operatively coupled to the device is configured to control the balloon to change the torsional moment of the device to increase a stability of the device within the accommodating ear canal conduit at the target area;
   wherein the processor is configured to change the elasticity of the stem by changing the stiffness of the electroactive polymer element; and
   increasing a stiffness of the device by selectively stiffening the balloon of the device upon reaching the target area within the accommodating ear canal conduit under control of the processor to fixate the device, wherein the balloon is an elliptical balloon when fully inflated prior to a deformation, where the elliptical balloon has an elliptical cross section in a plane perpendicular to an insertion direction, and
   wherein a torsion moment of the balloon is varied under control of the processor when the device is at the target area so as to stabilize the device.

2. The method of claim 1 wherein the processor controls introduction of the fluid into the balloon.

\* \* \* \* \*